United States Patent [19]
Sutherland et al.

[11] Patent Number: 5,337,209
[45] Date of Patent: Aug. 9, 1994

[54] HIGH ENERGY DENSITY LEAD MAGNESIUM NIOBATE-BASED DIELECTRIC CERAMIC AND PROCESS FOR THE PREPARATION THEREOF

[75] Inventors: Audrey E. Sutherland, Eldersburg, Md.; Keith Bridger, Washington, D.C.; Eric M. Fiore, Bel Air, Md.; Julie A. Christodoulou, Baltimore, Md.; Alex E. Bailey, Hampstead; Allan S. Gelb, Baltimore, both of Md.

[73] Assignee: Martin Marietta Corporation, Bethesda, Md.

[21] Appl. No.: 943,357

[22] Filed: Sep. 10, 1992

[51] Int. Cl.$^5$ .................. H01G 4/12; C04B 35/46
[52] U.S. Cl. .................. 361/321.5; 501/136; 501/137
[58] Field of Search ............... 361/321; 501/136, 137, 501/139, 152

[56] References Cited

U.S. PATENT DOCUMENTS

| | | | |
|---|---|---|---|
| 4,265,668 | 5/1981 | Fujiwara et al. | 106/73.3 |
| 4,339,544 | 7/1982 | Sakabe et al. | 501/136 |
| 4,536,821 | 8/1985 | Wheeler et al. | 361/321 |
| 4,542,107 | 9/1985 | Kato et al. | 501/134 |
| 4,724,511 | 2/1988 | Alexander et al. | 361/321 |
| 4,751,209 | 6/1988 | Yokotani et al. | 501/138 |
| 4,818,736 | 4/1989 | Yamashita et al. | 501/136 |
| 4,977,485 | 12/1990 | Mori et al. | 361/321 |
| 5,006,956 | 4/1991 | Kawakita et al. | 361/321 |
| 5,059,566 | 10/1991 | Kanai et al. | 501/138 |

FOREIGN PATENT DOCUMENTS

0202603 11/1984 Japan .................. 501/137

OTHER PUBLICATIONS

Guha et al, "Effect of Excess PbO on the Sintering Characteristics and Dielectric Properties of Pb(Mg$_{1/3}$Nb$_{2/3}$)O$_3$–PbTiO$_3$ Based Ceramics", Mar. 1988 J. Am. Ceram. Soc.

"Hot-Isostatic Pressing of PZT Materials", L. J. Bowen, W. A. Schulze and J. V. Biggers, *Power Metallurgy International*, vol. 12, No. 2, 1980, pp. 92 to 95.

*Primary Examiner*—Mark L. Bell
*Assistant Examiner*—Deborah Jones
*Attorney, Agent, or Firm*—Bruce M. Winchell; Brian J. Rees

[57] ABSTRACT

A dielectric ceramic composition is disclosed comprising lead magnesium niobate and strontium titanate, barium titanate or a combination thereof. Dopants such as Ta, La, Y, Eu, Nd, Sm, Gd, W, Si, Zr and Sb may also be included in the composition. The lead magnesium niobate with strontium titanate and/or barium titanate composition has been found to possess extremely favorable properties such as high dielectric constant, low dielectric loss, high breakdown strength, low field-induced strain, high electrical resistivity and exceptionally high energy storage capacity. A process is also disclosed for the production of dielectric ceramic materials which includes the use of hot isostatic pressing in an oxygen-containing atmosphere. The disclosed dielectric compositions are useful in capacitors for many applications, including medical devices such as defibrillators and pacemakers.

15 Claims, 4 Drawing Sheets

HIGH ENERGY DENSITY LEAD MAGNESIUM NIOBATE-BASED DIELECTRIC CERAMIC AND PROCESS FOR THE PREPARATION THEREOF

BACKGROUND OF THE INVENTION

The present invention relates to high energy density dielectric ceramics based on lead magnesium niobate (also known as PMN). More particularly, the dielectric ceramics comprise lead magnesium niobate with barium titanate (also known as BT) and/or strontium titanate (also known as ST) additions. Dopants such as tantalum, lanthanum, tungsten and the like may also be included. The dielectric ceramics possess extremely high energy densities and are useful in many applications, including medical devices such as defibrillators and pacemakers. The present invention also relates to a new method of preparing dielectric ceramics, including the use of hot isostatic pressing (HIPing) in an oxygen-containing atmosphere.

Dielectric materials used in ceramic capacitors must have characteristics such as high dielectric constant, low temperature coefficients in the dielectric constant and small dielectric loss. In addition, high energy density capacitors are required to have high permittivities that are relatively stable with temperature and field, high breakdown strengths and minimal field-induced strains.

A known ceramic having a high dielectric constant is barium titanate with additions of stannates, zirconates and other titanates. Strontium titanate and lead lanthanum zirconium titanate are also known as dielectric ceramics. Other conventional ceramics having high dielectric constants comprise solid solutions of lead-containing constituents such as lead magnesium niobate, lead zinc niobate and lead titanate. Examples of such compositions are given in U.S. Pat. Nos. 4,339,544 to Sakabe et al and 4,977,485 to Mori et al.

The methods of preparing conventional dielectric ceramics typically include the mixing of oxide starting materials, followed by sintering. In the manufacture of multilayer capacitors, a layer of metal paste is placed on a green sheet of the ceramic material. Several sheets are then stacked and fired to form the multilayer device. Since the dielectric ceramic and electrode metal are fired simultaneously, various attempts have been made to lower the sintering temperature of the ceramic in order to allow the use of relatively inexpensive electrode metals, such as Ag, instead of expensive, higher melting metals, such as Pt and Pd.

U.S. Pat. No. 4,818,736 to Yamashita et al discloses a high dielectric constant ceramic composition comprising lead zinc niobate, lead magnesium niobate and lead titanate in which a portion of the Pb site of the lead zinc niobate is substituted with Ba or Sr.

U.S. Pat. No. 5,059,566 to Kanai et al discloses a high dielectric constant composite material. One component of the composite may comprise lead zinc niobate, lead magnesium niobate and lead titanate, while the other component is a glass such as $B_2O_3$, $SiO_2$, $Al_2O_3$, BaO or MgO.

U.S. Pat. No. 4,724,511 to Alexander et al discloses a high dielectric constant ceramic composition comprising lead magnesium niobate, lead zinc niobate, lead zirconate, titanium dioxide and bismuth titanate, along with other oxide or rare earth additions.

U.S. Pat. No. 4,536,821 to Wheeler et al discloses a high dielectric constant ceramic composition comprising lead magnesium niobate, lead zinc niobate and an oxide such as silica, manganese dioxide, zinc oxide, nickel oxide, alumina, ceric oxide, lanthanum oxide, tungsten oxide, gallium oxide, titanium dioxide or lead oxide.

U.S. Pat. No. 4,265,668 to Fujiwara et al discloses a high dielectric constant ceramic composition comprising lead magnesium niobate, lead titanate and, optionally, other oxides such as lead manganese tungstate or lead manganese niobate. A portion of the lead may be replaced with Ba, Sr or Ca.

U.S. Pat. No. 4,542,107 to Kato et al discloses a dielectric ceramic composition comprising lead magnesium niobate, lead zinc niobate and lead iron tungstate, with minor additions of manganese oxide.

U.S. Pat. Nos. 4,751,209 to Yokotani et al and 5,006,956 to Kawakita et al disclose high dielectric constant ceramic compositions comprising lead magnesium niobate, lead nickel tungstate and lead titanate, with additions of either metals such as Ca, Ba and Sr or oxides such as PbO and NiO.

The dielectric ceramic compositions cited above are not considered useful for high energy density capacitor use. Conventional high energy density capacitors typically have energy densities of about 1 $J/cm^3$ and include liquid impregnated polymer film capacitors for high voltage applications and electrolytic capacitors for low voltage applications.

The present invention has been developed in view of the foregoing and to overcome the deficiencies of the prior art.

SUMMARY OF THE INVENTION

An object of the present invention is to provide a new high energy density dielectric ceramic material. The ceramic is based on lead magnesium niobate with additions of barium titanate, strontium titanate, or combinations thereof. Dopants such as Ta, La, W, Nd, Y, Eu, Sm, Gd, Si, Zr and Sn may also be included. In addition to extremely high energy density, the dielectric ceramic exhibits very low strain and very high electrical strength.

Another object of the present invention is to provide a new method of preparing a dielectric ceramic. The method includes the use of hot isostatic pressing in an oxygen-containing atmosphere to produce a substantially flaw free dielectric material having high electrical resistivity.

Another object of the present invention is to provide a high energy density capacitor incorporating a lead magnesium niobate-based dielectric ceramic material.

DETAILED DESCRIPTION OF THE INVENTION

Figure 1:
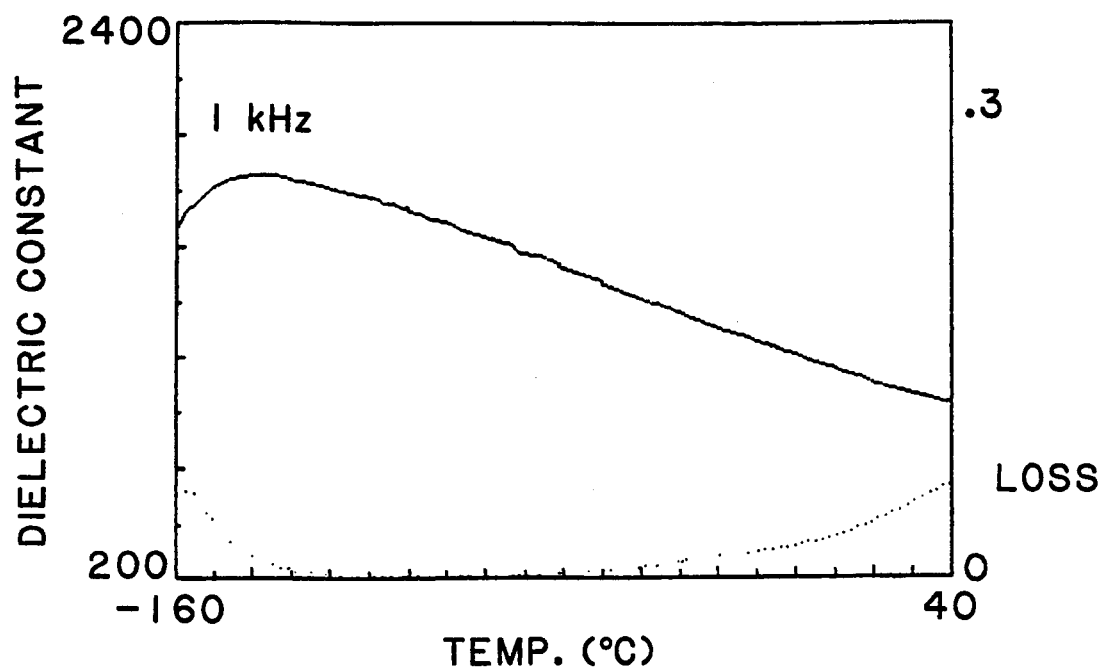
FIGS. 1-5 show dielectric constant and loss as a function of temperature for various dielectric ceramic compositions of the present invention.

In accordance with the present invention, dielectric compositions are produced comprising lead magnesium niobate ($Pb(Mg_xNb_y)O_3$) and barium titanate ($BaTiO_3$), strontium titanate ($SrTiO_3$), or a combination thereof. In addition, dopants such as Ta, La, Y, Eu, Nd, Sm, Gd, W, Si, Zr and Sb may be added to the compositions. The addition of rare-earth dopants, for example, may cause a drop in the Curie temperature and a broadening of the dielectric properties over temperature. Preferred dopants include Ta, La, Y and Eu because they exhibit a pronounced effect on dielectric properties. It is noted that the nomenclature $Pb(Mg_xNb_y)O_3$ as used herein is meant to include stoichiometric lead magnesium niobate ($Pb(Mg_{\frac{1}{3}}Nb_{\frac{2}{3}})O_3$) as well as non-stoichiometric lead magnesium niobate (e.g., $Pb(Mg_{\frac{1}{2}}Nb_{\frac{1}{2}})O_3$). While stoichiometric lead magnesium nipbate is the most preferred embodiment, it should be understood that non-stoichiometric lead magnesium nipbate is within the scope of the present invention.

The $Pb(Mg_xNb_y)O_3$ preferably ranges from about 50 to about 85 mole percent and more preferably ranges from about 60 to about 80 mole percent of the composition. A most preferred $Pb(Mg_xNb_y)O_3$ range is from about 60 to 70 mole percent, while 70 mole percent is a particularly preferred amount. The $SrTiO_3$ or $BaTiO_3$ preferably ranges from about 15 to about 50 mole percent and more preferably ranges from about 20 to about 40 mole percent. A more preferred $SrTiO_3$ or $BaTiO_3$ range is from about 30 to 40 mole percent, while 30 mole percent is a particularly preferred amount. The dopant, if it is a Ta substitution for Nb on the "B" site, may range from 0 to about 50 mole percent and preferably from about 10 to 40 mole percent. Other dopants may range from 0 to about 5 mole percent and preferably from about 0.1 to 3 mole percent, with 1 mole percent being a particularly preferred amount.

Table 1 illustrates the preferred, more preferred and most preferred compositional ranges of the present invention. The ranges of dopants given are for elements such as La, W, Nd, Y, Eu, Sm, Gd, Si, Zr and Sb.

TABLE 1

| | Compositional Ranges (mole percent) | | |
|---|---|---|---|
| | $Pb(Mg_xNb_y)O_3$ | $SrTiO_3$ and/or $BaTiO_3$ | Dopant |
| Preferred | 50–85 | 15–50 | 0–5 |
| More Preferred | 60–80 | 20–40 | 0–5 |
| Most Preferred | 60–70 | 30–40 | 0.1–3 |

The dielectric compositions of the present invention are obtained by the basic steps of mixing starting oxides, calcining, pressing, sintering and hot isostatically pressing. In the preferred embodiment, starting powders of MgO and $Nb_2O_5$ are weighed in stoichiometric proportions, then excess MgO is added in order to scavenge impurities. The powders are mixed in a ball mill in Freon 113 and then dried. Other solvents such as isopropanol may be used in place of the Freon 113. The powders are calcined at temperatures ranging from about 1000° to about 1100° C., with a temperature of about 1000° C. being preferred. Calcining times may range from about 3 to about 15 hours, with a time of about 15 hours being preferred. Next, PbO, $TiO_2$ and dopant, if dopant is desired, are mixed together with either $SrCO_3$ or $BaCO_3$ in stoichiometric proportions. Either barium carbonate or strontium carbonate may be utilized depending upon which of barium or strontium titanate is desired in the final dielectric composition. The powders are then mixed by milling again in Freon 113. The powders are calcined at temperatures ranging from about 750° to about 850° C., with a temperature of about 800° C. being preferred. Calcining times may range from about 1 to about 3 hours, with a time of about 3 hours being preferred.

Next, the powders are milled again for particle size reduction, dried and die pressed to form pellets at a pressure ranging from about 5000 to about 10,000 psi, with a pressure of approximately 5000 psi being preferred. The pellets are then isostatically pressed at room temperature at a pressure ranging from about 35,000 psi to about 45,000 psi, with a pressure of approximately 45,000 psi being preferred.

Before sintering, the pellets are packed in powder of approximately the same composition in closed $Al_2O_3$ crucibles. They are then heated with temperature increasing at a rate ranging from about 400° to about 600° C. per hour, with a heating rate of approximately 600° C. per hour being preferred. The samples are held at 1000° to 1200° C. for about 1 to 5 hours, with a temperature of about 1185° C. and a time of approximately 3 hours being preferred. Sintering temperatures may be lowered by the use of selected dopants. For example, Ta additions may be used to lower the sintering temperature. The samples are then cooled at a rate ranging from about 400° to about 600° C. per hour, with a cooling rate of about 480° C. per hour being preferred.

Next, the samples are hot isostatically pressed at a temperature ranging from about 900° to about 1200° C. and a pressure of from about 25,000 to about 30,000 psi, with a hold time of from about 1 to about 3 hours and an atmosphere of from about 5 to about 10 percent oxygen. The procedure of hot isostatic pressing in an oxygen-containing atmosphere has been found to improve the breakdown strength of the compositions of the present invention as it substantially eliminates material flaws which contribute to poor breakdown strengths. For example, hot isostatically pressed samples of the present invention with La additions have been found not to breakdown at fields of 65 MV/m. It should be recognized that the use of oxygen hot isostatic pressing is not limited to the specific lead magnesium niobate-containing compositions disclosed herein, but is also applicable to other dielectric lead-based ceramic compositions having a perovskite structure. Thus, in accordance with the present invention, the use of oxygen HIPing is possible for a broad range of lead-based oxide materials.

The compositions set forth in Tables 2a and 2b were prepared in accordance with the present invention.

TABLE 2a

| Composition No. | Formula | % Perovskite Phase (cubic) |
|---|---|---|
| 1 | 0.70 $Pb(Mg_xNb_y)O_3$—0.30 $SrTiO_3$ | 99 |
| 2 | 0.60 $Pb(Mg_xNb_y)O_3$—0.40 $SrTiO_3$ | 100 |

TABLE 2b

| Composition No. | Formula | % Perovskite Phase (cubic) |
|---|---|---|
| 3 | $0.80[(Pb_{.99}La_{.01})(Mg_{\frac{1}{3}}Nb_{\frac{2}{3}})_{.9975-.0025}O_3]$—$0.20SrTiO_3$ | 97 |
| 4 | $0.70[(Pb_{.99}La_{.01})(Mg_{\frac{1}{3}}Nb_{\frac{2}{3}})_{.9975-.0025}O_3]$—$0.30SrTiO_3$ | 98 |

TABLE 2b-continued

| Composition No. | Formula | % Perovskite Phase (cubic) |
|---|---|---|
| 5 | $0.60[(Pb_{.99}La_{.01})(Mg_{\frac{1}{3}}Nb_{\frac{2}{3}})_{.9975-.0025}O_3]-0.40SrTiO_3$ | 100 |

After sintering the compositions recited in Tables 2a and 2b phase purity was determined by X-ray diffraction. All compositions were primarily a cubic perovskite phase, i.e., 97 percent or greater, with very small amounts of a second pyrochlore phase. The sample densities achieved after sintering ranged from 92–98% of theoretical density. After hot isostatic pressing in an oxygen-containing atmosphere, the compositions typically have densities of 99–100% of theoretical density. The oxygen HIPed compositions have been found to have extremely low porosity and flaw concentrations, and in some instances may be optically transparent.

In accordance with the present invention, the use of hot isostatic pressing in an oxygen-containing atmosphere has been found not only to reduce flaws and increase density of the ceramic, but also to prevent the formation of oxygen vacancies. Oxygen vacancies are to be avoided because they significantly lower the resistivity of the ceramic, particularly under high dielectric fields. Absent the use of an oxygen-containing atmosphere in the HIPing process, the resultant ceramics possess significantly lower resistivities. Thus, oxygen HIPing produces highly dense ceramics having exceptionally high electrical resistivity even under high electric fields.

FIGS. 1 through 5 show low field permittivity and loss as a function of temperature for typical dielectric compositions of the present invention. As can be seen in these Figures, the compositions of the present invention possess the favorable properties of high dielectric constant, low temperature coefficients in the dielectric constant and low dielectric loss.

The following examples illustrate various aspects of the present invention. The examples are not meant to limit the scope of the invention.

EXAMPLE 1

A dielectric ceramic material having the composition $0.70Pb(Mg_xNb_y)O_3-0.30SrTiO_3$ (Composition 1) was produced in the following manner. Starting powders of MgO and $Nb_2O_5$ of 99.5 and 99.999% purity, respectively, were weighed in stoichiometric proportions, then 1.5 weight percent excess MgO was added. The powders were mixed in a ball mill in Freon 113, dried, calcined at 1100° C. for 15 hours, and then milled again for particle size reduction. Next, PbO and $TiO_2$ of 99.999% purity were mixed together with $SrCO_3$ of 99.999% purity in stoichiometric proportions.

The powders were then mixed by milling again in Freon 113. The powder was calcined at 800° C. for 3 hours, milled again for particle size reduction, dried, die pressed to 10,000 psi to form pellets which were then isostatically pressed to 45,000 psi. Before sintering, the pellets were packed in powder of the same composition in closed $Al_2O_3$ crucibles. They were then heated with temperature increasing at a rate of 600° C. per hour, until a temperature of 1185° C. was reached. The samples were held at that temperature for 3 hours and then they were cooled with temperature decreasing at a rate of 600° C. per hour.

Select samples were hot isostatically pressed at 1100° C. under 5% oxygen to 27,000 psi. After hot isostatic pressing, sample densities averaged 99–100% of theoretical density and some of the samples were optically transparent, an indication of low porosity and flaw concentration. Samples tested were 1–3 mm thick. Field-induced strains were measured with a linear variable displacement transducer (LVDT) at 1 MV/m. High field measurements were done on samples that were electroded with thermally evaporated Cr (1000Å) and Au (5000 Å).

From each batch, several samples had marginless electrodes in order to more accurately measure relative permittivity, and several samples were electroded with 2-mm margins, where the electrode diameter was less than the sample diameter, in order to more accurately measure high-field properties. Stainless steel contact pins were silver-epoxied to the center of the electrodes and the samples were encapsulated in Hysol epoxy resin and cured at 20° C. for 24 hours. High-field relative permittivity and tan(delta) were measured by ac-ripple (i-V technique) and dc leakage current was measured directly using an electrometer (Keithley). The ac-ripple technique allows measurement of capacitance and loss current at a high electric field. These measurements are used to calculate relative permittivity and tan(delta). The dc leakage current was used to calculate resistivity and tan(delta) at high electric fields.

Samples were tested with DC fields at a temperature of 20° C. for relative permittivity and breakdown strengths. The samples were immersed in oil during high electric field measurements of breakdown strengths. The results are shown in Tables 3 and 4. Table 3 tabulates the Curie temperatures measured at 100 Hz and the microstrain measured at 1 MV/m. Table 4 shows relative permittivity at various electric field strengths. FIG. 1 shows dielectric constant and loss at various temperatures for Composition 1.

EXAMPLE 2

Figure 2:
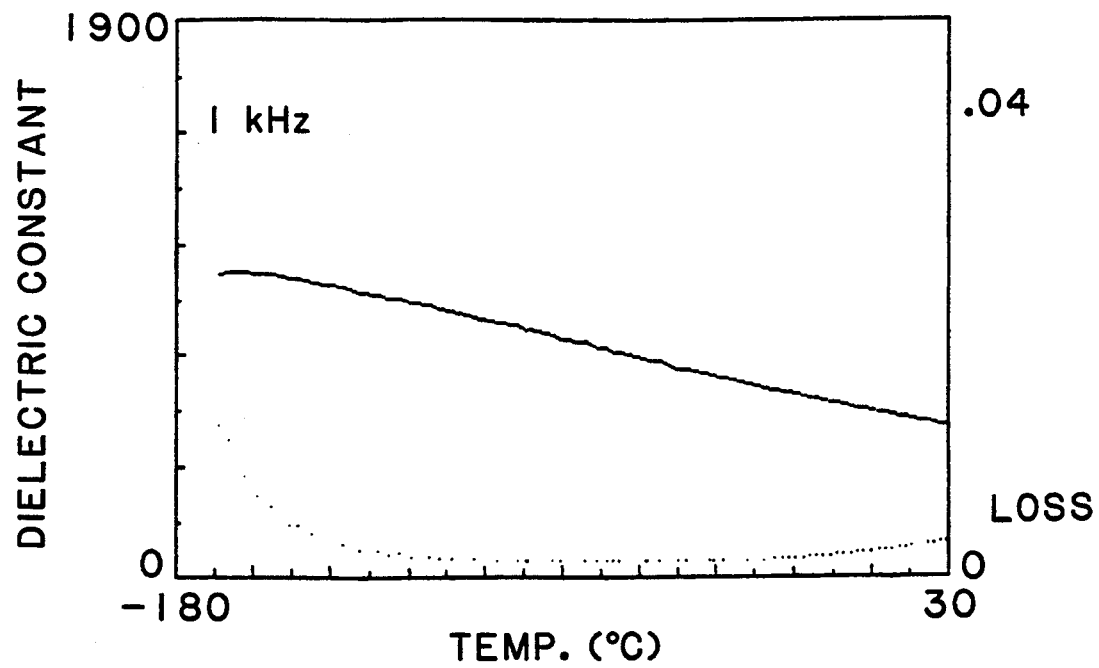

Example 1 is repeated, with the exception that the amounts of $Pb(Mg_xNb_y)O_3$ and $SrTiO_3$ are adjusted to produce a $0.60 Pb(Mg_xNb_y)O_3 0.40 SrTiO_3$ composition (Composition 2). The resultant dielectric ceramic material exhibits favorable microstrain and Curie temperature values as shown in Table 3. FIG. 2 shows dielectric constant and loss at various temperatures for Composition 2.

EXAMPLE 3

A dielectric ceramic material of the composition $0.80[(Pb_{0.99}La_{0.01})(Mg_{\frac{1}{3}}Nb_{170})_{0.9975-0.0025}O_3]-0.20SrTiO_3$ (Composition 3) is produced in the following manner. Starting powders of MgO and $Nb_2O_5$ of 99.5 and 99,999% purity, respectively, were weighed in stoichiometric proportions, then 1.5 weight percent excess MgO was added. The powders were mixed in a ball mill in Freon 113, dried, calcined at 1100° C. for 15 hours, and then milled again for particle size reduction. Next, PbO, $TiO_2$, $SrCO_3$ and La dopant of 99.999% purity were mixed together in stoichiometric proportions. The powders were then mixed by milling again in Freon 113.

The powder was calcined at 800° C. for 3 hours, milled again for particle size reduction, dried, die pressed to 10,000 psi to form pellets which were then isostatically pressed to 45,000 psi. Before sintering, the pellets were packed in powder of the same composition in closed $Al_2O_3$ crucibles. They were then heated with temperature increasing at a rate of 600° C. per hour, until a temperature of 1185° C. was reached. The samples were held at that temperature for 3 hours and then cooled with the temperature decreasing at a rate of 600° C. per hour.

Select samples were hot isostatically pressed at 1100° C. under 5% oxygen at 27,000 psi. After hot isostatic pressing, sample densities averaged 99–100% of theoretical density and some of the samples were optically transparent, an indication of low porosity and flaw concentration. Samples tested were 1–3 mm thick. Field-induced strains were measured with a linear variable displacement transducer (LVDT) at 1 MV/m. High field measurements were done on samples that were electroded with thermally evaporated Cr (1000A) and Au (5000 A).

From each batch, several samples had marginless electrodes in order to more accurately measure relative permittivity, and several samples were electroded with 2-mm margins, where the electrode diameter was less than the sample diameter, in order to more accurately measure high-field properties. Stainless steal contact pins were silver-epoxied to the center of the electrodes and the samples were encapsulated in Hysol epoxy resin and cured at 20° C. for 24 hours.

High-field relative permittivity and tan (delta) were measured by ac-ripple (i-V technique) and dc leakage current was measured directly using an electrometer (Keithley). The ac-ripple technique allows measurement of capacitance and loss current at a high electric field. These measurements are used to calculate relative permittivity and tan(delta). The dc leakage current was used to calculate resistivity and tan(delta) at high electric fields.

Figure 3:
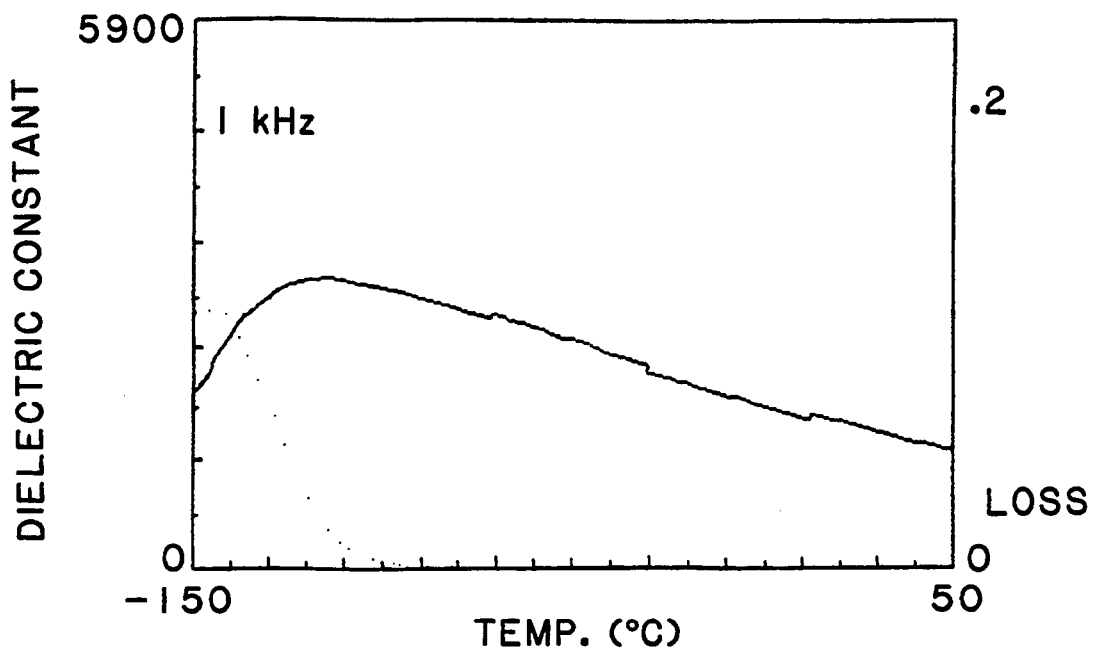

Samples were tested with DC fields at a temperature of 20° C. for relative permittivity and breakdown strengths. The samples were immersed in oil during high electric field measurements of breakdown strengths. The results are shown in Tables 3 and 4. Table 3 lists Curie temperature and microstrain values, while Table 4 lists relative permittivity at various fields and breakdown strengths. FIG. 3 shows dielectric constant and loss at various temperatures for Composition 3.

EXAMPLE 4

Figure 4:
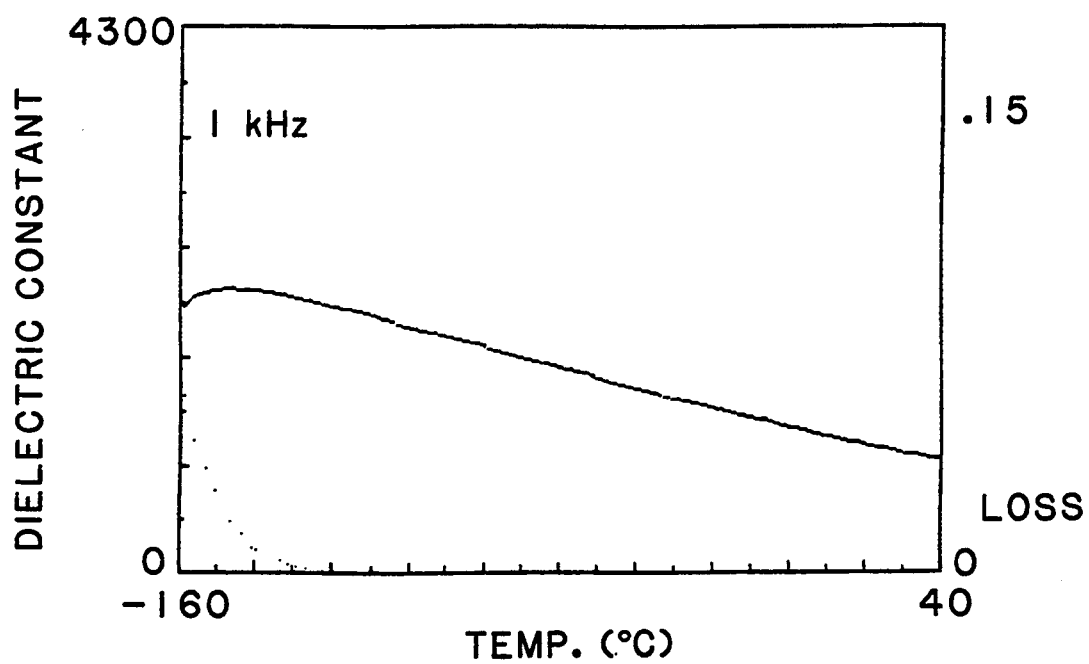
Figure 6:
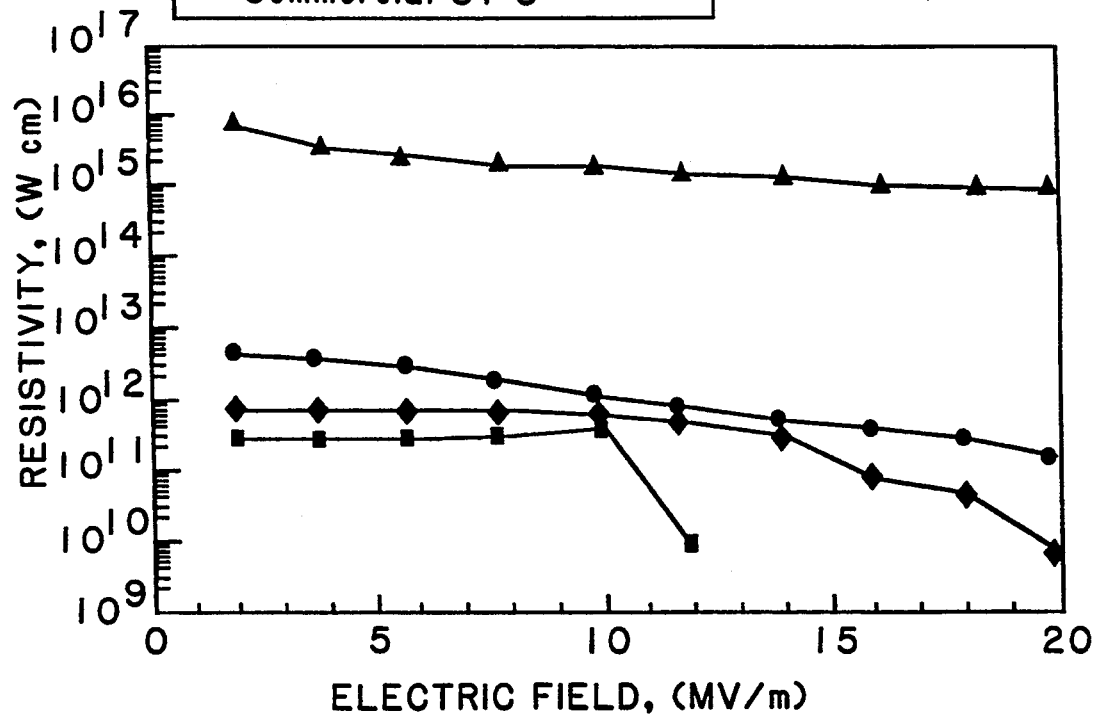
FIG. 6 shows the improved electrical resistivity of a present composition at various electric fields compared to conventional compositions.

Example 3 is repeated, with the exception that the amounts of $Pb(Mg_xNb_y)O_3$ and $SrTiO_3$ are adjusted to produce a $0.70[Pb_{0.99}La_{0.01})Mg_{\frac{1}{3}}Nb_{\frac{2}{3}})_{0.9975-0.0025}O_3]-0.30SrTiO_3$ composition (Composition 4). The resultant dielectric ceramic material exhibits favorable microstrain, Curie temperature, relative permittivity and breakdown field values as shown in Tables 3 and 4. FIG. 4 shows dielectric constant and loss at various temperatures for Composition 4. FIG. 6 shows the resistivity of the Composition 4 material compared to commercial strontium titanate formulations. Even at 20 MV/m the Composition 4 material has a resistivity of $10^{15}$ ohm-cm, giving it an insulation resistance of greater than 40,000 ohm-F.

EXAMPLE 5

Figure 5:
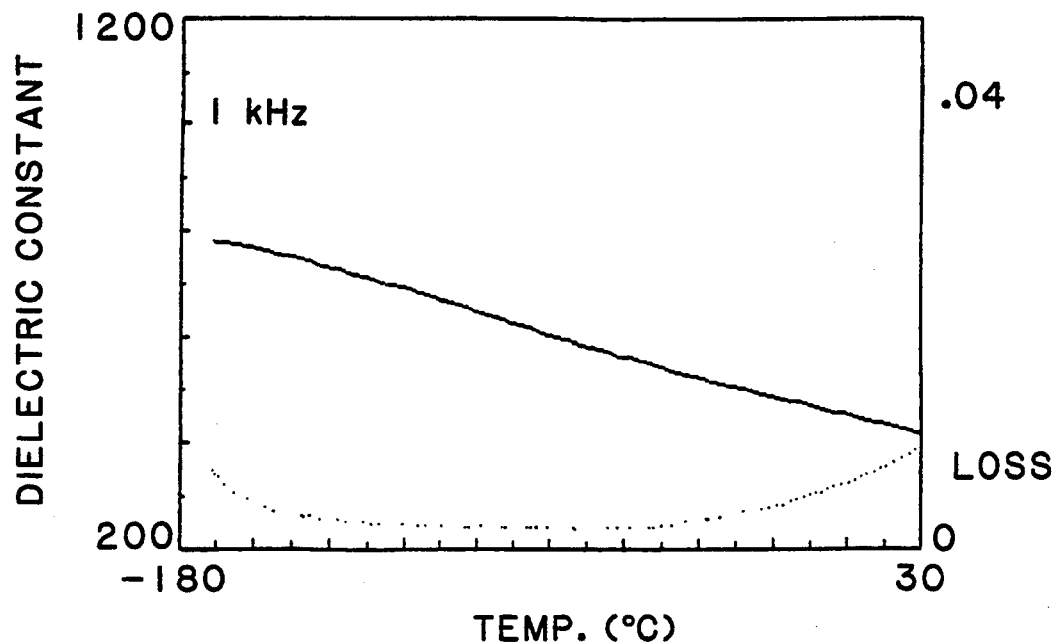

Example 3 is repeated, except that the amounts of $Pb(Mg_xNb_y)O_3$ and $SrTiO_3$ are adjusted to produce a $0.60[(Pb_{0.99}La_{0.01})(Mg_{\frac{1}{3}}Nb_{\frac{2}{3}})_{0.9975-0.002503}O_3]-0.40SrTiO_3$ composition (Composition 5). The resultant dielectric ceramic material exhibits favorable microstrain, Curie temperature relative permittivity and breakdown field values as shown in Tables 3 and 4. FIG. 5 shows dielectric constant and loss at various temperatures for Composition 5.

TABLE 3

| Curie Temperature and Microstrain | | |
| --- | --- | --- |
| Composition No. | Tc at 1 kHz | Microstrain at 1 MV/m |
| 1 | −140 | 0 |
| 2 | −163 | 0 |
| 3 | −114 | 0 |
| 4 | −146 | 0 |
| 5 | −170 | 0 |

As can be seen from Table 3, the addition of increasing amounts of $SrTiO_3$ lowers the Curie temperature. A similar result would be achieved with $BaTiO_3$ additions. A low Curie temperature is desirable in order to obtain low field-induced strains near room temperature. Near the Curie temperature, field-induced strains are at a maximum due to piezoelectric and electrostrictive effects. Table 3 also shows that the compositions of Examples 1–5 of the present invention possess relatively low Curie temperatures, ranging from −114° to −170° C. These low Curie temperatures contribute to the low field-induced strain values of the compositions at room temperature. The low field-induced strain achieved with the present dielectric compositions is important to prevent tensile stresses when energized and mechanical fatigue under cyclic loading. Field-induced strain is particularly to be avoided in multilayer capacitor designs because such strain of the dielectric material is likely to induce mechanical and/or fatigue failure of the dielectric/electrode interface.

TABLE 4

| Relative Permittivity and Breakdown Field | | | | |
| --- | --- | --- | --- | --- |
| | Relative Permittivity at various field strengths | | | Breakdown Field |
| Composition | 0 MV/m | 10 MV/m | 20 MV/m | MV/m |
| 1 | 1100 | 900 | | |
| 3 | 1750 | 1200 | 690 | >65 |
| 4 | 970 | 780 | 560 | >65 |
| 5 | 700 | 640 | 540 | >65 |

As demonstrated in Table 4, the compositions of the present invention demonstrate a high relative permittivity at various field strengths. Relative permittivity of the present compositions varies with electric field. For example, the relative permittivity of Composition 4 varies from about 970 to 568 as the electric field strength varies from 0 to 20 MV/m. As can be seen in Table 4, the compositions of the present invention exhibit high breakdown strengths, with break down occurring at an electric field of greater than 65 MV/m in Compositions 3, 4 and 5.

The combination of high relative permittivity, high breakdown strength and nominal field-induced strain possessed by the present compositions permits them to be used for a large range of applications because they have a higher energy storage capacity than conventional dielectric materials. Table 5 compares typical values of density, relative permittivity, breakdown field and energy storage capacity of Composition 4 to typical values of conventional dielectric ceramics.

TABLE 5

Dielectric Properties of Conventional Ceramics Versus Composition 4 of the Present Invention

| Material | Density (g/cm$^3$) | Relative Permittivity at 10 MV/m | Breakdown Field (MV/m) | Energy Stored (J/cm$^3$) |
|---|---|---|---|---|
| SrTiO$_3$[a] | 5.13 | 210 | 40 | 1.3 |
| BaTiO$_3$[b] | 6.02 | 700 | 10 | 0.4 |
| BaTiO$_3$[c] | 6.02 | 500 | 40 | 1.7 |
| PLZT[d] | 7.62 | 1200 | 30 | 3.1 |
| Composition 4 | 6.5 | 780 | >65 | 6.7 |

[a]Commercial formulation Ticon S
[b]Commercial Z5U formulation
[c]Commercial X7R formulation
[d]Pb$_{1-x}$La$_x$Zr$_y$Ti$_z$O$_3$ As can be seen from Table 5, Composition 4 suprisingly demonstrates a higher energy storage capacity, approximately 6.7 J/cm$^3$, and a high breadkdown field, greater than 65 MV/m, while maintaining a high relative permittivity as compared to conventional dielectrics. According to the present invention, capacitors made from the presently disclosed compositions typically possess energy storage capacities of greater than 3 J/cm3 and preferably greater than 5 J/cm$^3$.

The dielectric ceramics of the present invention can be used for prior art applications such as multi-layered capacitors, and other capacitors. These capacitors may be formed by any of the conventional forming techniques. One such technique of manufacturing a multilayer ceramic capacitor using the dielectric compositions of the present invention may comprise the steps of screen printing a plurality of conductive metal ink electrodes on each of a plurality of unfired dielectric sheets; assembling a stack of such sheets with the electrodes of alternate layers arranged relative to one another as appropriate to the particular construction employed, for example sideways stepped or overlapping crosswise; pressing the sheets together with extra blank ceramic sheets applied to the top and bottom of the stack if required; cutting the sheets to form individual capacitor components; and cold isostatically pressing and firing the individual components. Subsequently the electrodes between every other sheet may be connected in a conventional manner (end terminated) by the appropriate application of conductive paint to opposite end (side) faces of the stack. The energy storage capacity of such capacitors may be varied by adjusting the geometry of the device. For example, the use of thinner layers of dielectric ceramic material and/or thinner electrode layers results in greater breakdown strength and higher energy storage capacity for a given volume.

Additionally, the new dielectric ceramics of the present invention can be utilized in many different areas never before possible, due primarily to their high relative permittivity and breakdown strength. Thus, a higher capacity for energy storage at high field strengths is realized. Such applications include medical implants such as pacemakers, defibrillators and combinations thereof, electric guns, low frequency-high power transducers, and high-power microwave devices. As a specific example, the dielectric ceramics of the present invention may be incorporated in a capacitor for use in an automatic implantable cardioverter defibrillator unit (AICD). This list of potential applications should not be considered to be totally inclusive, but rather representative of uses for the present dielectric compositions.

Figures 7A, 7B:
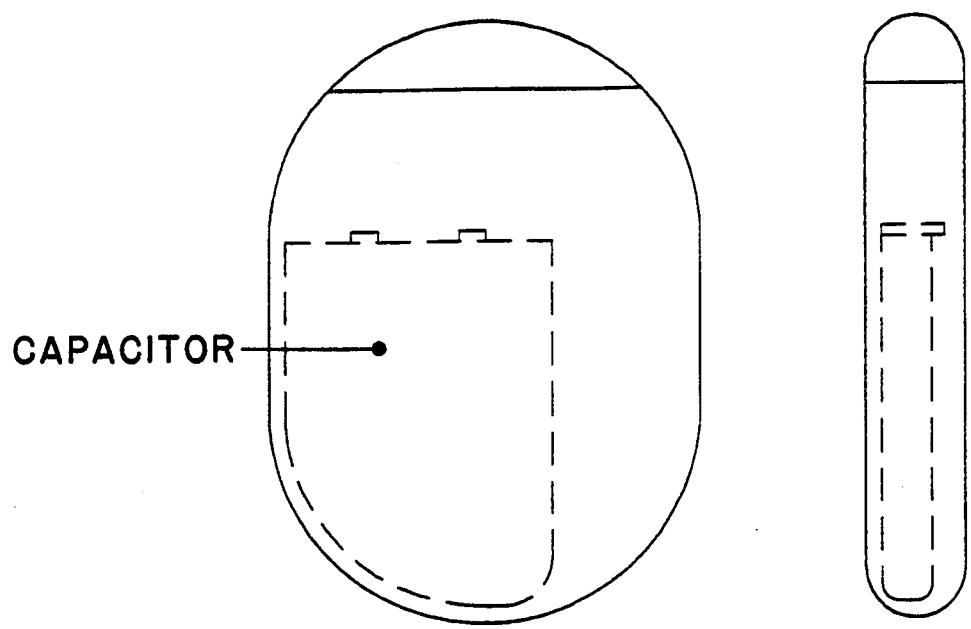
FIGS. 7a and 7b are two views of a schematic drawing of an implantable defibrillator incorporating a capacitor made of a dielectric ceramic of the present invention.

Of importance, is the use of compositions hereinbefore described comprising Pb(Hg$_x$Nb$_y$)O$_3$, BaTiO$_3$, and SrTiO$_3$, or combinations thereof in the forming of capacitors incorporated within defibrillators in general, but particularly adaptable for implantable defibrillators. Volume efficiency is of great Importance in the field of implantable defibrillators since the insert cavity is of limited size. As is to be understood, prior art capacitors used in implantable defibrillators have been generally cylindrical in contour and provide for disadvantageous volume constraints. Through use of the hereinbefore described compositions and methods of forming same, capacitors may be shaped to achieve a volume efficiency unknown in the prior art. Capacitors may be formed in generally flattened configurations or other contours amenable to the interior volume space available for implantable defibrillators for insert into a restricted cavity volume in general and particularly into a mammalian cavity. FIG. 7 schematically illustrates one such configuration wherein the capacitor is depicted by dashed lines and comprises the presently disclosed ceramic composition. As can be seen, the implantable defibrillator has a flattened, disk-like shape that is advantageous for implantation compared to prior art cylindrical configurations.

While the present invention has been disclosed in its preferred embodiments, it is to be understood that the invention is not limited to the precise disclosure contained herein, but may otherwise be embodied with various changes, modifications and improvements which may occur to those skilled in the art, without departing from the spirit and scope of the invention as defined in the following claims.

What is claimed is:

1. A dielectric composition comprising a solid solution of from about 50 to about 85 mole percent Pb(Mg$_x$Nb$_y$)O$_3$ wherein x is $\frac{1}{3}$, y is $\frac{2}{3}$ or x is $\frac{1}{2}$, y is $\frac{1}{2}$, and from about 15 to about 50 mole percent SrTiO$_3$, BaTiO$_3$ or combination thereof.

2. A dielectric composition according to claim 1, wherein the SrTiO$_3$, BaTiO$_3$ or combination thereof comprises from about 20 to about 40 mole percent of the composition.

3. A dielectric composition according to claim 1, wherein the SrTiO$_3$, BaTiO$_3$ or combination thereof comprises about 30 mole percent of the composition.

4. A dielectric composition according to claim 1, wherein the composition further comprises up to about 50 mole percent Ta dopant.

5. A dielectric composition according to claim 4, wherein the Ta dopant comprises from about 10 to about 40 mole percent of the composition.

6. A dielectric composition according to claim 1, wherein the composition further comprises up to about 5 mole percent of at least one dopant selected from La, Y, Eu, Nd, Sm, Gd, W, Si, Zr and Sb.

7. A dielectric composition according to claim 6, wherein the dopant is selected from La, Y and Eu.

8. A dielectric composition according to claim 6, wherein the dopant comprises from about 0.1 to about 3 mole percent of the composition.

9. A dielectric composition according to claim 1, wherein the Pb(Mg$_x$Nb$_y$)O$_3$ is stoichiometric Pb(Mg$_{\frac{1}{3}}$Nb$_{\frac{2}{3}}$)O$_3$.

10. A dielectric composition according to claim 1, wherein the Pb(Mg$_x$Nb$_y$)O$_3$ is non-stoichiometric Pb(Mg$_{\frac{1}{2}}$Nb$_{\frac{1}{2}}$)O$_3$.

11. A dielectric composition according to claim 1, wherein the composition is primarily a perovskite phase.

12. A capacitor comprising electrodes in contact with at least one layer of dielectric material, the dielectric material comprising from about 50 to about 85 mole percent stoichometric or non-stoichiometric $Pb(Mg_xNb_y)O_3{}^3$ and from about 15 to about 50 mole percent $SrTiO_3$, $BaTiO_3$ or combination thereof.

13. A capacitor according to claim 12, wherein the capacitor comprises multiple layers of the dielectric material separated by electrode layers.

14. A capacitor according to claim 12, wherein the capacitor possesses an energy storage capacity of greater than 3 $J/cm^3$.

15. A capacitor according to claim 12, wherein the capacitor possesses an energy storage capacity of greater than 5 $J/cm^3$.

* * * * *

UNITED STATES PATENT AND TRADEMARK OFFICE
CERTIFICATE OF CORRECTION

PATENT NO. : 5,337,209  Page 1 of 2
DATED : August 9, 1994
INVENTOR(S) : Audrey E. Sutherland et al It is certified that error appears in the above-indentified patent and that said Letters Patent is hereby corrected as shown below:

Column 3, line 19, change "nipbate" to --niobate--; line 21, change "nipbate" to --niobate--; line 31, change "$BaTiO_3$-" to --$BaTiO_3$--.

Column 5, line 22, change "tn" to --in--; line 24, change "al so" to --also--.

Column 6, line 43, "0.60 $Pb(Mg_xNB_y)O_3 0.40$" should read --0.60 $Pb(Mg_xNB_y)O_3$-0.40--;

lines 52 and 53, "0.80[$(Pb_{0.99}La_{0.01})(Mg_{1/3}Nb_{170})_{0.9975-0.0025}O_3$]-0.20$SrTiO_3$" should read --0.80[$(Pb_{0.99}La_{0.01})(Mg_{1/3}Nb_{2/3})_{0.9975-0.0025}O_3$]-0.20$SrTiO_3$--;

line 55, "99,999%" should read --99.999%--.

Column 7, line 23, change "steal" to --steel--; line 27, change "tan (delta) to --tan(delta)--; line 50 change "$O_3$_" to --$O_3$--; line 66; change "0.60[$(Pb_{0.99}La_{0.0\ 1})(Mg_{1/3}Nb_{2/3})_{0.9975-0.002503}O_3$]" to --0.60[$(Pb_{0.99}La_{0.01})(Mg_{1/3}Nb_{2/3})_{0.9975-0.0025}O_3$]--.

UNITED STATES PATENT AND TRADEMARK OFFICE
CERTIFICATE OF CORRECTION

PATENT NO. : 5,337,209

DATED : August 9, 1994

INVENTOR(S) : Audrey E. Sutherland et al

It is certified that error appears in the above-indentified patent and that said Letters Patent is hereby corrected as shown below:

Column 9, line 23, "$J/cm_3$" should read --$J/cm^3$--; line 68, "$Pb(Hg_xNb_y)O_3$," should read --$Pb(Mg_xNb_y)O_3$,--.

Column 11, line 8, delete "$Pb(Mg_xNb_y)O_3^3$" and add --$Pb(Mg_xNb_y)O_3$ wherein x is 1/3, y is 2/3 or x is 1/2, y is 1/2,--.

Signed and Sealed this

Nineteenth Day of December, 1995

BRUCE LEHMAN

Attest:

Attesting Officer

Commissioner of Patents and Trademarks